US 7,757,183 B2
Jul. 13, 2010

(12) United States Patent
Rutledge et al.

(54) TIMING ADAPTIVE PATIENT PARAMETER ACQUISITION AND DISPLAY SYSTEM AND METHOD

(75) Inventors: Jolyn Rutledge, Amesbury, MA (US); Judith Shaffer, Orchard Park, NY (US); Amy M. Manetta, North Billerica, MA (US); Mark Penny, Salem, MA (US)

(73) Assignee: Draeger Medical Systems, Inc., Andover, MA (US)

( * ) Notice: Subject to any disclaimer, the term of this patent is extended or adjusted under 35 U.S.C. 154(b) by 2147 days.

(21) Appl. No.: 10/414,064

(22) Filed: Apr. 15, 2003

(65) Prior Publication Data
US 2003/0218630 A1    Nov. 27, 2003

Related U.S. Application Data

(60) Provisional application No. 60/374,912, filed on Apr. 23, 2002.

(51) Int. Cl.
 G06F 3/048 (2006.01)
 G06F 17/00 (2006.01)
 G06F 3/00 (2006.01)
 G06Q 10/00 (2006.01)

(52) U.S. Cl. .................. 715/781; 715/764; 715/738; 705/2

(58) Field of Classification Search .............. 705/2
See application file for complete search history.

(56) References Cited

U.S. PATENT DOCUMENTS

| | | | | |
|---|---|---|---|---|
| 4,878,175 A | * | 10/1989 | Norden-Paul et al. | 705/2 |
| 5,253,361 A | * | 10/1993 | Thurman et al. | 707/3 |
| 5,361,202 A | | 11/1994 | Doue | 364/413.01 |
| 5,970,466 A | * | 10/1999 | Detjen et al. | 705/8 |
| 6,074,345 A | * | 6/2000 | van Oostrom et al. | 600/300 |
| 6,188,407 B1 | | 2/2001 | Smith et al. | 345/353 |
| 6,198,695 B1 | | 3/2001 | Kirton et al. | 368/10 |
| 6,243,095 B1 | | 6/2001 | Shile et al. | 345/357 |
| 6,353,436 B1 | | 3/2002 | Reichlen | 345/427 |
| 6,434,572 B2 | | 8/2002 | Derzay et al. | 707/104.1 |
| 2002/0099477 A1 | | 7/2002 | Wallace et al. | 700/299 |
| 2002/0109735 A1 | | 8/2002 | Chang et al. | 345/853 |

(Continued)

FOREIGN PATENT DOCUMENTS

WO    WO98/29790    7/1998

OTHER PUBLICATIONS

Chelewski, Paula K., Designing a patient-care 24-hour flowsheet, Apr. 1998, Nursing Management Chicago, vol. 29, Iss 4; p. 37.*

*Primary Examiner*—William L Bashore
*Assistant Examiner*—Jordany Núñez
(74) *Attorney, Agent, or Firm*—Jack Schwartz & Associates, PLLC

(57) ABSTRACT

A system and a method are described for allowing a user to generate a timeline and display patient data with varying time intervals. The time intervals can range from a few minutes to several hours. By allowing a user to select start time and end time when a time interval change occurs, the time interval change is applied to a selected portion or duration of the timeline rather than the full length. Also multiple time intervals may be selected and applied to the patient data.

25 Claims, 6 Drawing Sheets

U.S. PATENT DOCUMENTS

2002/0116225 A1 8/2002 Morse et al. .................... 705/3
2002/0165437 A1 11/2002 Chen .......................... 600/300
2002/0186243 A1 12/2002 Ellis et al. ................... 345/753

* cited by examiner

TIMING ADAPTIVE PATIENT PARAMETER ACQUISITION AND DISPLAY SYSTEM AND METHOD

CROSS REFERENCE TO RELATED APPLICATION

This application claims the benefit of a provisional U.S. application, U.S. Ser. No. 60/374,912, filed Apr. 23, 2002, in the names of the present inventors.

FIELD OF THE INVENTION

The present invention generally relates to a system and a method for processing and displaying of medical information, and more particularly, to processing and displaying of patient data. In one exemplary aspect, the present invention enables a user of a charting system to create an adaptive timeline for display of patient data.

BACKGROUND OF THE INVENTION

In today's medical environment, various patient data is generated during a patient's stay in a hospital. The patient data is either stored electronically or written down on paper, depending on types of data and level of automation for a particular hospital. The type of data may include parameter settings for a piece of medical equipment used to treat a patient or parameter values obtained relating to physiology of a patient.

For example, various types of medical equipment are used to monitor or administer care to patients in different hospital departments. In a critical care unit, a ventilator is frequently used to ventilate a patient's lungs with breathing gas when the patient's ability to breathe on his or her own is impaired. In order to properly administer ventilation, a caregiver needs to first set up various settings for the ventilator. Examples of commonly required settings to control a ventilator include: Peak Inspiratory Pressure (PIP) setting for limiting the peak pressure during inspiration of air; and Positive End Expiratory Pressure (PEEP) setting for limiting the peak pressure at the end of expiration of air. Many other ventilator settings may also be controlled, depending on the capability of the particular ventilator.

Likewise, medical equipment may also be equipped with various physiological sensors so that the condition of a patient may be monitored. For example, commonly monitored parameters for a ventilator include Mean Airway Pressure (MAP) for indicating the mean pressure measured within the airway during the breathing cycle, and Tidal Volume Inspired (TVi) for measuring volume of gas inhaled by a patient during a normal breath. Of course, other different patient parameters may be monitored by other types of medical devices.

In addition, hospitals also have laboratories to analyze, for example, blood of a patient. The results of the blood tests may be printed out by a lab technician and given to a caregiver or entered electronically on a computer to be accessed by the caregiver. The caregiver can then analyze the results and choose a correct course of treatment for the patient.

The various exemplary patient data for a patient during his or her stay is now frequently stored electronically and often in a networked environment. A care provider may then access the data using, for example, web browser software through a network. This allows a caregiver to access the data throughout the hospital or even remotely through Internet.

SUMMARY OF THE INVENTION

The present inventors recognize that during a patient's stay in a hospital, the patient's vital signs are collected at different rates depending on, for example, the health of the patient. In particular, if the patient's vital signs are tracked on a paper flow sheet, the data is likely to be written down using time intervals at which the data has been collected by a caregiver. It is therefore desirable to have a variable time interval capability for an electronic patient charting system that allows hospitals to convert patient data from paper to digital storage.

Although previous systems may allow the time interval to be adjusted, the change is applied to the entire length of the patient's stay. By universally changing the time interval, prior systems display either too much or too little data for some portion of the patient's record. In contrast, the present invention allows resulting patient record to reflect data as a caretaker would have written it. Thus, during a critical period, the caretaker is free to concentrate on the patient knowing that data will be correctly entered on the patient's flow sheet later. When the crisis is over, the caretaker can select the appropriate time interval for that critical time period or duration. At that point, data is automatically collected and copied into the patient record efficiently.

Therefore, in one exemplary aspect of the present invention, a system and a method for processing medical information are described. A user is allowed to select a time interval applicable to a timeline on a patient data screen. A user is also allowed to select a start time and an end time identifying a duration for which the selected time interval is applicable. Patient data is then displayed with the timeline such that the selected time interval is used for the duration between the selected start time and the selected end time.

DETAILED DESCRIPTION

Figure 1:
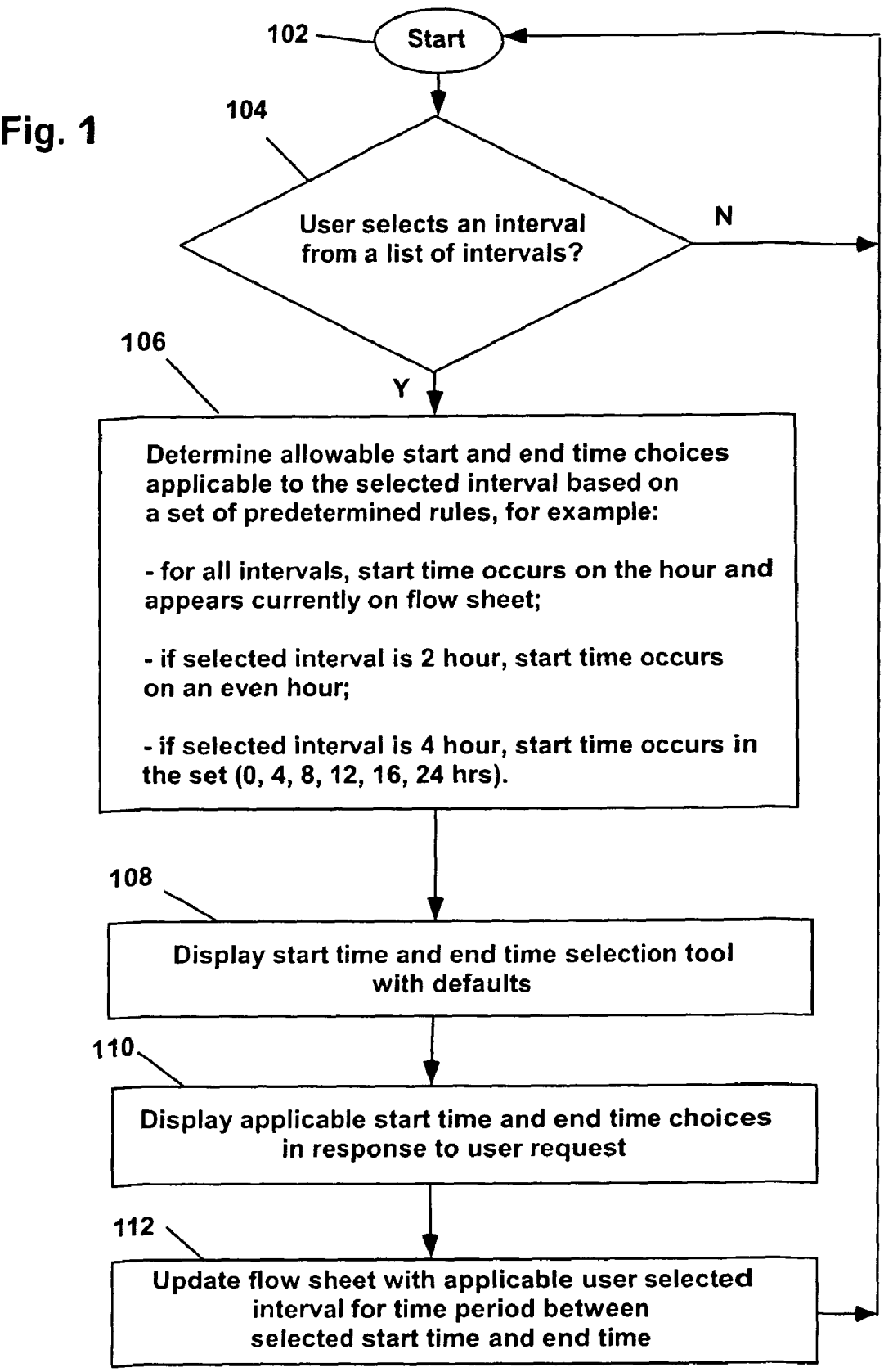
FIG. 1 is an exemplary process according to the present invention.
Figure 2:
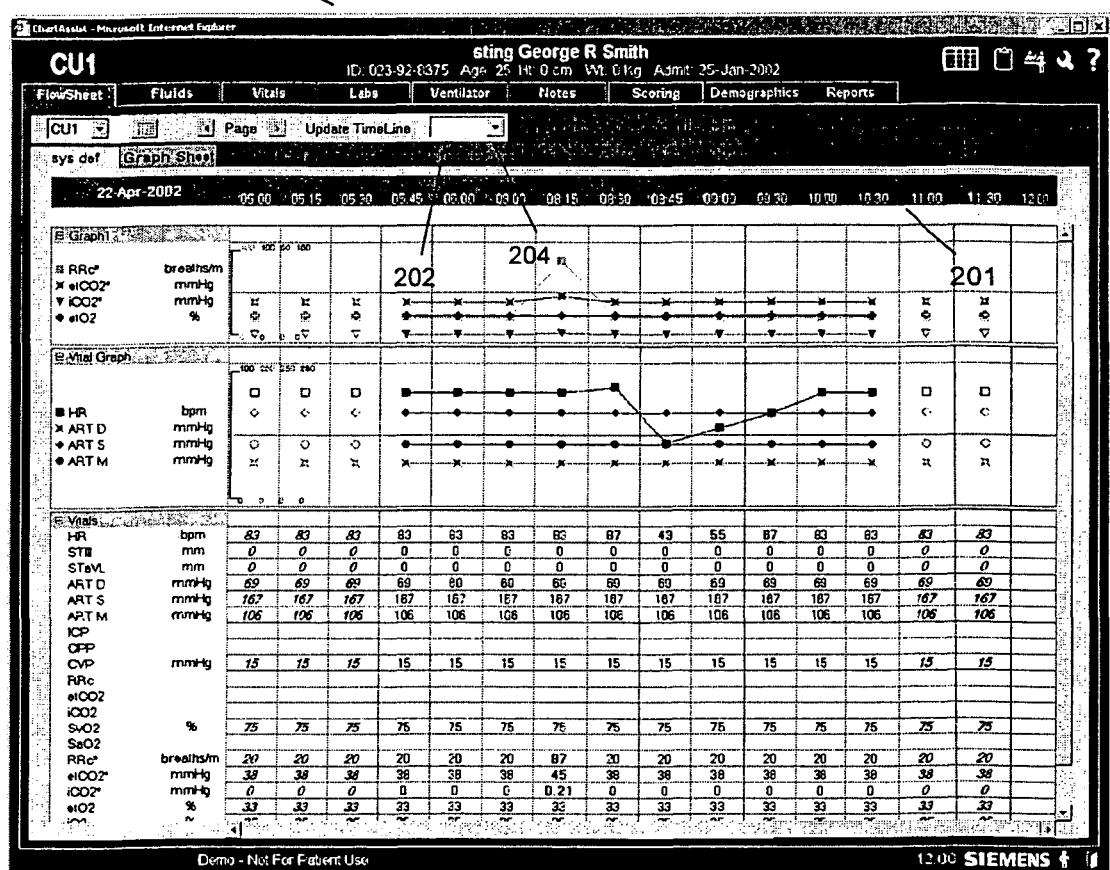
FIG. 2 shows an example of a user interface screen according to the present invention.

FIG. 1 shows an exemplary method employed by a system for processing and displaying patient data according to the present invention. FIG. 2 shows an exemplary user interface screen for a patient flow sheet which may be employed by the present system. An exemplary patient flow sheet or patient chart 200 in FIG. 2 comprises a timeline 201. The timeline 201 is divided into time intervals for displaying patient data in each time interval. In this example, the timeline 201 is divided into 15-minute intervals as shown in FIG. 2.

According to the principles of the present invention, the present system allows a user to select a time interval for a timeline via a list of available intervals, at step 104 of FIG. 1.

A user may select an interval from, for example, a user interface popup icon 202 of flow sheet display screen 200 of FIG. 2. For example, when a user selects a down arrow 204 of FIG. 2, a list of available intervals is displayed. An exemplary list of available intervals (not shown) may comprise intervals such as 3 minutes, 5 minutes, 15 minutes, 30 minutes, 1 hour, 2 hours, 4 hours, etc.

Once a time interval is selected at step 104 of FIG. 1, the system determines in step 106 which allowable start time and end time choices are applicable to the selected interval on the flow sheet based on a predetermined set of rules. The determination of allowable start time and end time choices is based at least in part on the interval chosen at step 104 and the time currently being displayed on the flow sheet. An example of a predetermined set of rules for presenting applicable start and end time choices to a user may be:

1) for all intervals, change or start time occurs on the hour;
2) if the selected interval is a 2 hour interval, the change or start time needs to occur on an even hour;
3) if the selected interval is a 4 hour interval, the change or the start hour needs to be in the set of. (0:00, 4:00, 8:00, 12:00, 16:00, and 20:00);
4) in order for an hour to be a candidate for the start time, it needs to currently appear on the flow sheet being used.

In general, the purpose of these rules is to create a timeline that is logical and understandable to the user, while protecting the integrity of patient data. For example, the last rule above applies to disallow certain user selections in the following way, when a flow sheet is being displayed with a 4-hour interval. In that case, if the hours currently shown on the flow sheet are 4:00, 8:00, and 12:00, the user may not choose to switch to a 1-hour interval at 11:00 because this would cause a discontinuity in the data. Also, the interval between 8 and 11 is three hours, and that is not a valid interval for the example given.

In addition, if the time interval has changed in the middle of the hour to a 1-hour mode, none of the columns following the change would occur on the hour, if not for the rules. It is unlikely that the user has intended this result when 1-hour mode has been selected. Therefore, the present system incorporates rules for presenting patient data in a flow sheet that further enhances user actions.

Once the system determines the applicable start and end times based on a set of predetermined rules as shown in step 106 of FIG. 1, the system allows a user to select a particular start time and a particular end time at steps 108 and 110 of FIG. 1.

At step 108 of FIG. 1, the system provides default settings for the start time and the end time. For example, as shown in an exemplary user screen 300 of FIG. 3, a start time and end time selection tool 304 is displayed when the user selects an interval. The selection tool 304 is populated with a predetermined default start time and a predetermined default end time 306 and 308 respectively, when the selection tool 304 is first displayed.

The allowable default start time is also governed by the predetermined rules as described in connection with step 106 of FIG. 1. For example, as shown in flow sheet screen 300 of FIG. 3, the default start time is the current time (i.e., now). When this is restricted by the exemplary set of predetermined rules, the default start time of now becomes "11:00" as shown in 306 of FIG. 3. This is because the user-selected interval for this default start time is "15 Minutes" as shown in 312 of FIG. 3, and the current time for flow sheet 300 is "11:56" as shown in 310 of FIG. 3.

Figure 3:
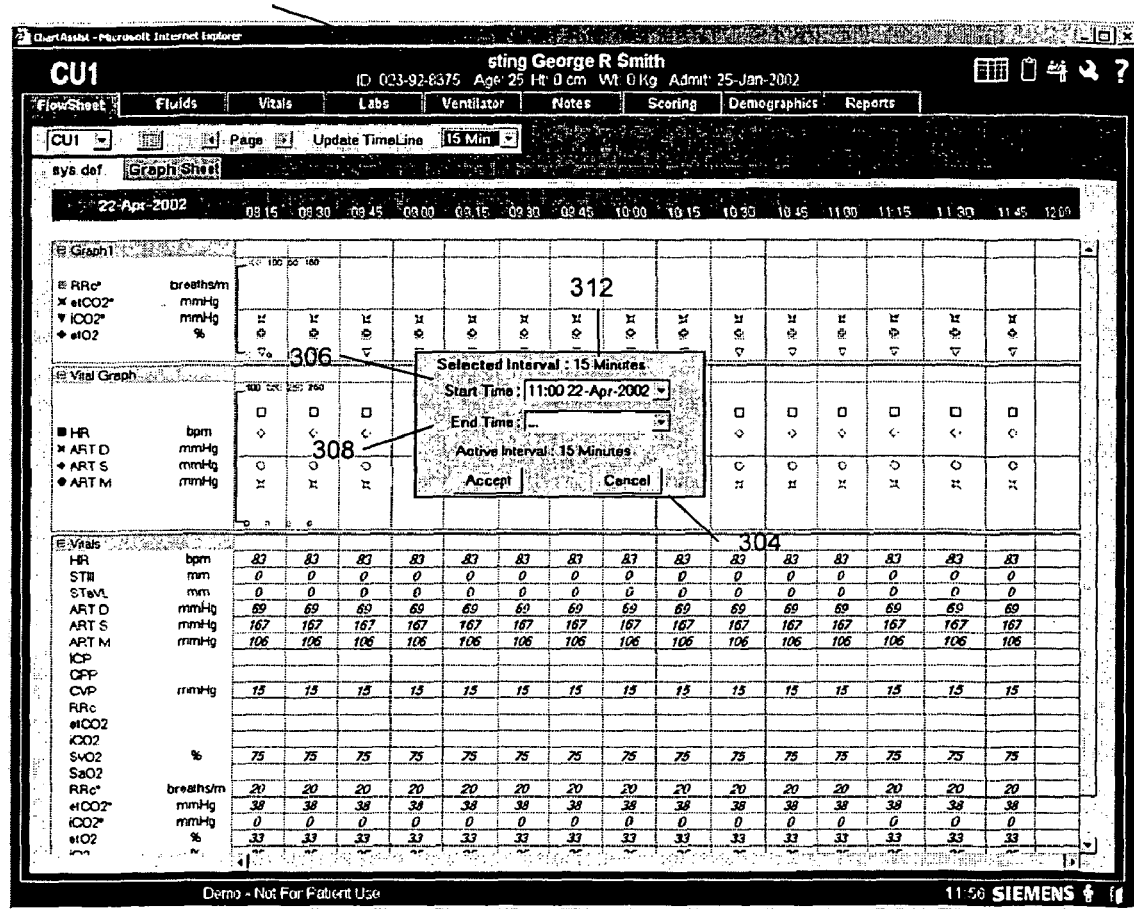
FIG. 3 is another example of a user interface screen having a start time and end time selection tool.

An example of a default end time shown in FIG. 3 is a blank entry 308 indicating that the default end time for applying the selected time interval is indefinitely extended into the future. Therefore, if the user accepts the exemplary default values as shown in selection tool 304 of FIG. 3, the time interval change takes place from now into the future until the settings are changed.

Additionally, the present system provides a list of available start time and end time choices automatically for a user. At step 110 of FIG. 1, the system displays all allowable start time and end time choices in response to a user request. This is illustrated in an exemplary flow sheet screen 400 of FIG. 4. For example, once a user selects a down arrow 404 of FIG. 4, a pop up screen 406 will be displayed with a list of the allowable start times as determined by, for example, the rules described at step 106 of the exemplary process flow of FIG. 1.

Figure 4:
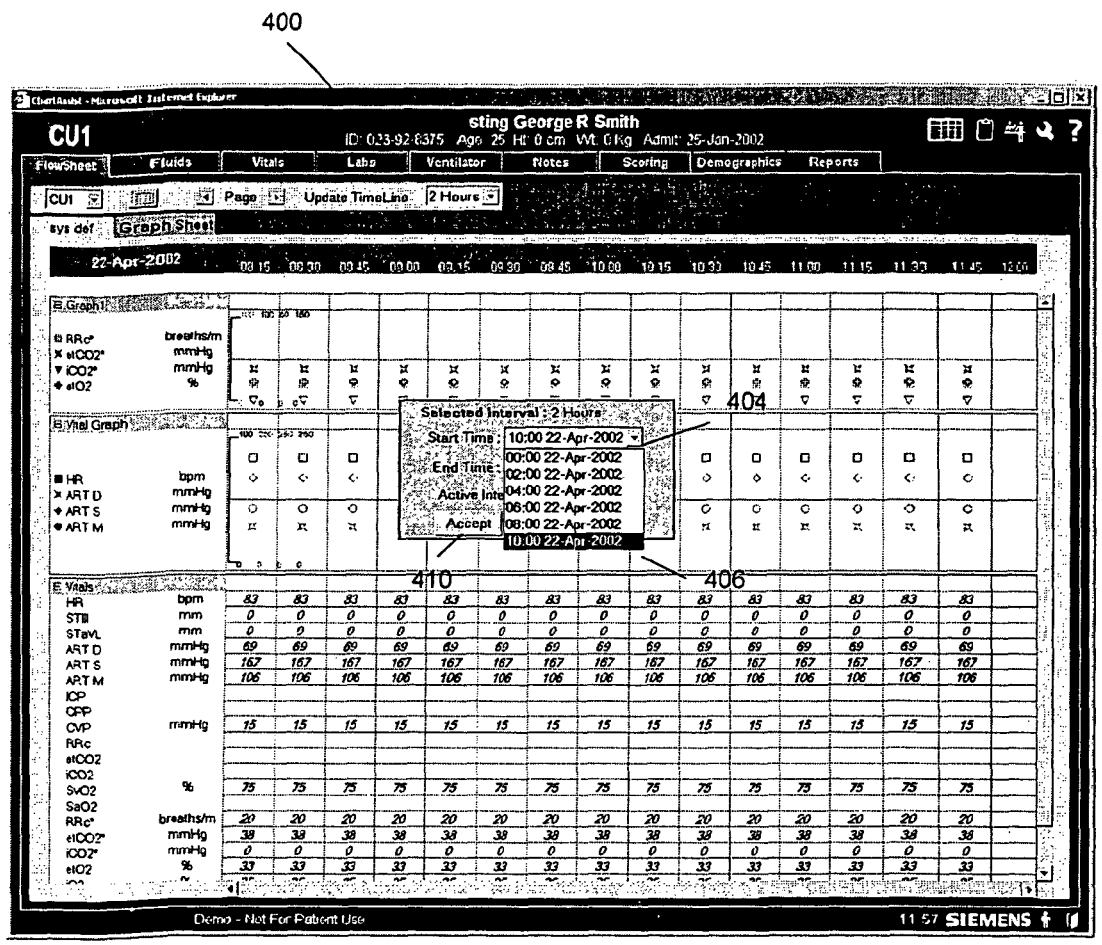
FIG. 4 is a user interface screen showing a list of applicable start time choices in response to a user request.

At step 112 of FIG. 1, the user may accept the start time and end time choices selected by the user by clicking on, for example, "Accept" icon 410 of FIG. 4. The selected interval change occurs for the timeline between the accepted start time and end time.

Using the same or similar sequence as described in steps 104 to 112 of FIG. 1, a user may select another interval to be applied to a duration or time period between a different start time and end time of the timeline. This allows the system to display patient data using one or more intervals on the same timeline.

Whenever an interval change involves the past, the data shown in a flow sheet changes. If the interval is decreased, more patient data is charted, and if the interval is increased some data is removed from the chart. When additional patient data is required, it may be gathered from a raw data pool in the system database, and the chart is automatically filled in.

Figure 5:
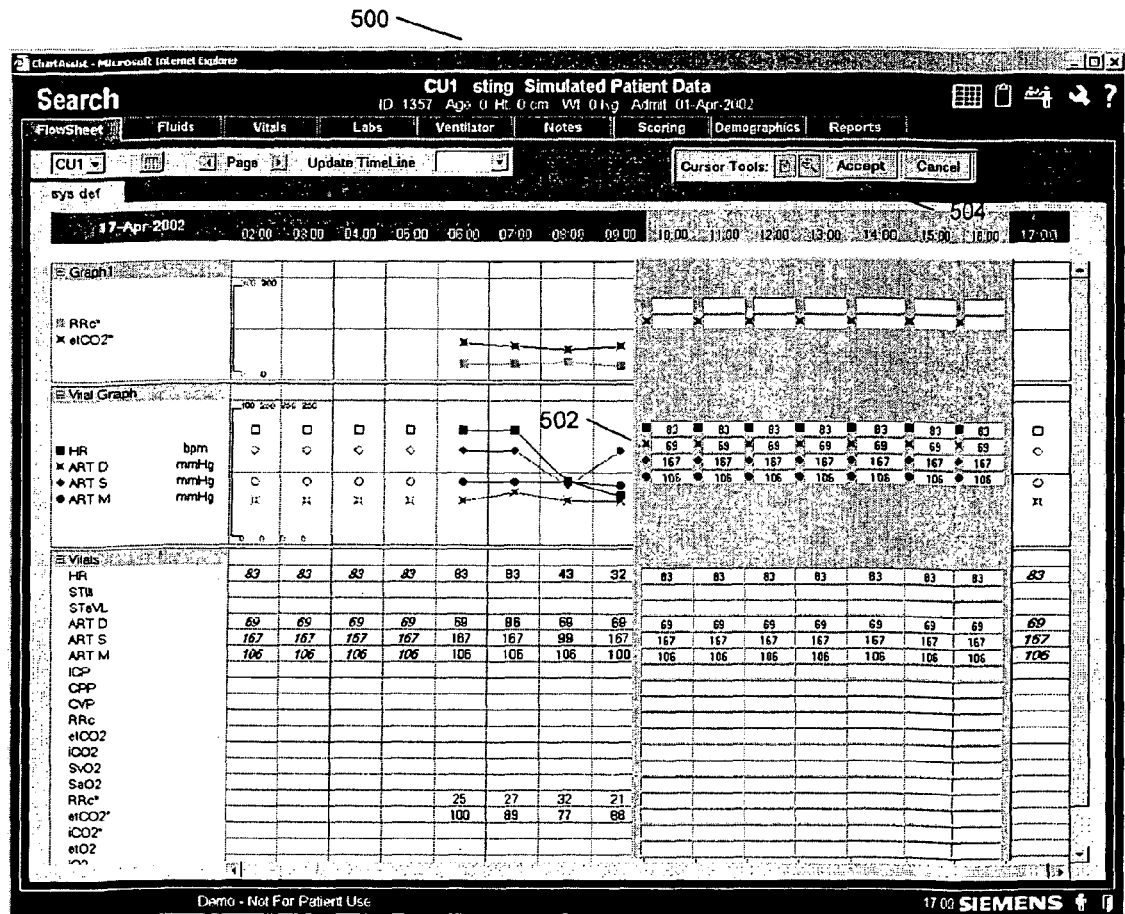
FIG. 5 is a user interface screen showing a tool for accepting data edits, changes and validation.

One function of a patient chart or flow sheet is to allow the user to edit, change and/or validate patient data. This process is shown in an exemplary flow sheet display 500 of FIG. 5. As shown in FIG. 5, a user may highlight a portion of the flow sheet 500 with a user selection tool such as a cursor (not shown). Once the portion of the data is highlighted, an edit screen 502 is displayed which allows the user to examine and change if necessary the values of patient data. Once the user has examined and/or changed the data, the user can then select "Accept" icon 504 to indicate that the user has validated the data.

In one aspect of the present invention, if data on a flow sheet has been edited, changed, and/or validated, the system assumes that it would be incorrect to remove that portion of the data from the chart. Therefore, one advantage of the present invention is to protect the user from inadvertently removing accepted data. The potential removal of data can occur for example, when a user changes a 1-hour interval to a 4-hour interval. Therefore, one embodiment of the present system automatically determines if an interval change requested would remove data that has been changed and/or validated. If that is the case, the interval change requested is ignored by the system, and a message is displayed which explains the problem to the user.

For data that has not been changed or accepted, there is no issue in removing the data from the chart. The data still resides in a raw data pool elsewhere in the system database either locally or remotely in a server.

Figure 6:
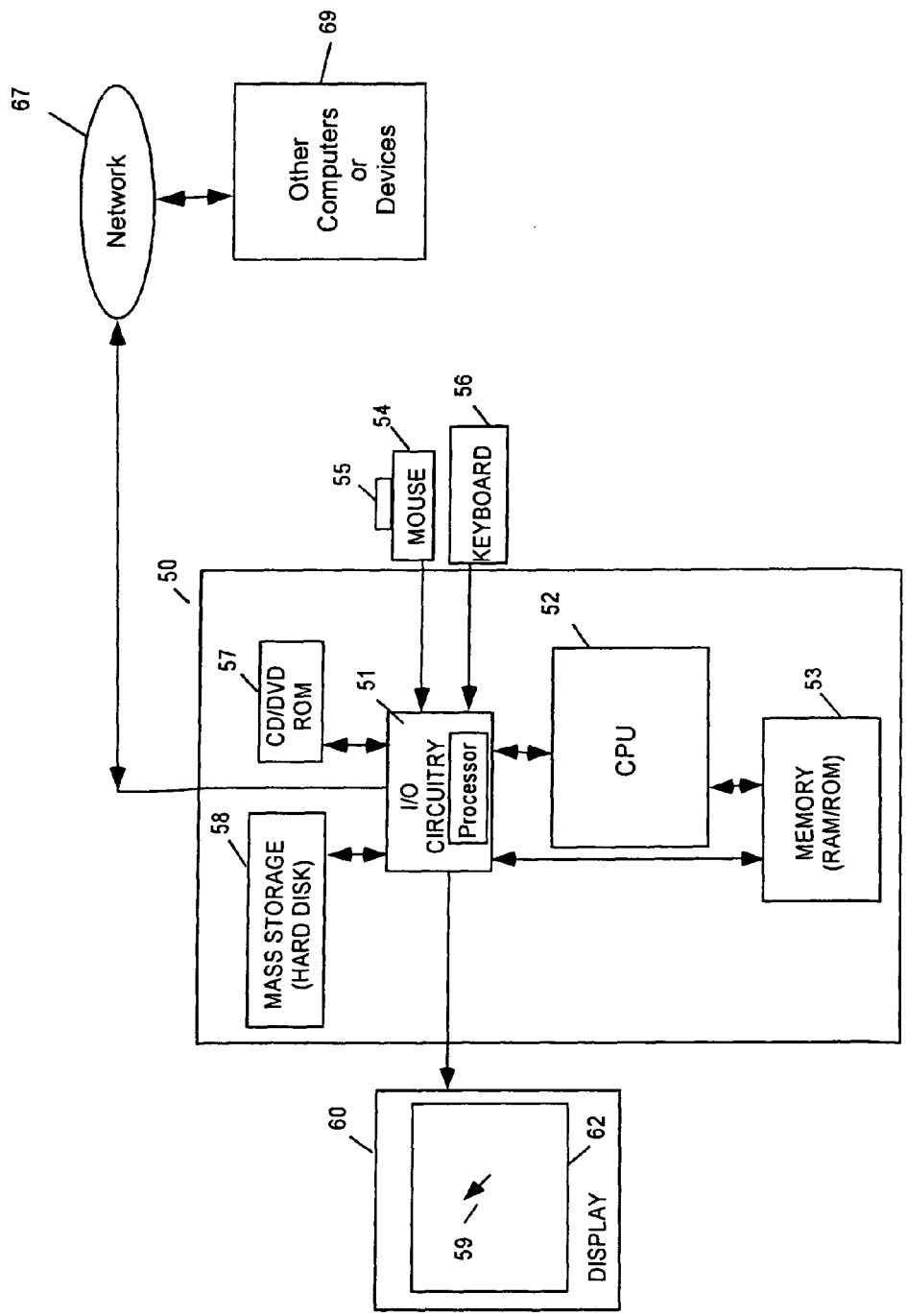
FIG. 6 is an exemplary system according to the present invention.

FIG. 6 describes an exemplary system in accordance with the present invention. System 50 may comprise a general purpose computer or a specially constructed computer. A general purpose or specially constructed computer may be used with a program or programs in accordance with the teachings herein. An example of general purpose computer may be an Intel® based personal computer, capable of running MS Windows®. An example of a specialized machine may be a patient data display system for used in a hospital.

The exemplary process of the present invention as shown in FIG. 1 may be implemented using an exemplary system illustrated in FIG. 6. System 50 of FIG. 6 comprises an input/output (I/O) section 51 which is used to communicate information in an appropriate form to and from other components of system 50. I/O section 51 may also communicate with a local area or wide are network 67, including the Internet, via for example, TCP/IP protocol. This allows system 50 to communicate with other computers or devices 69 over the network 67, via for example, a web browsing software such as Microsoft Internet Explorer®.

In addition, system 50 comprises a central processing unit (CPU) 52 coupled to I/O section 51, and a memory 53 such as RAM and/or ROM for storing computer programs and other information to be executed. An example of a computer program which may be executed by system 50 is a process illustrated in FIG. 1.

System 50 includes a display 60, such as, for example, a CRT monitor, a liquid crystal display (LCD), or others. As illustrated in FIG. 6, a user interface screen 62 is displayed on display 60. An example of a display screen 62 is shown, for example, as display screen 200 of FIG. 2 or screen 300 of FIG. 3.

System 50 further includes a cursor control 54, such as, for example, a mouse, a track ball, joystick or other device for selectively positioning a cursor 59 on a display screen 62 of the display 60. Typically, cursor control 54 includes a signal generator, such as a switch 55 which a user of the computer system may use to generate signals directing the computer to execute certain commands which have been focused or enabled by the cursor control 54. System 50 also includes a keyboard 56 to input data and commands from a user, as is well known in the art.

Also shown in FIG. 6 is a mass storage device 58, such as a hard disk, coupled to I/O circuit 51 to provide additional storage capability for computer 50. In addition, a CD/DVD ROM 57 is further coupled to I/O circuit 50 for additional storage capacity or as another I/O device. It will be appreciated that additional devices (not shown) may be coupled to computer 50 for various purposes, as well known in the art.

The described system and method may be advantageously applied to any system, including a web-based system, needing to display data with variable time granularity. There are no other restrictions on how often a time interval changes may occur. The user can always update the timeline, even if it has been previously changed. The described variable interval timeline system may be applied to any data that is displayed on a timeline. One aspect of the system is its ability to display data on a timeline where different time intervals that are shown concurrently for patient data. Another aspect is the system ability to change a patient chart's timeline interval in the past and the future.

It is to be understood that the embodiments and variations shown and described herein are for illustrations only and that various modifications may be implemented by those skilled in the art without departing from the scope of the invention.

The invention claimed is:

1. A method for processing medical information, comprising the steps of:
enabling a user via a user interface display image, to select a first periodic time interval for periodically displaying patient data in a first time duration on a timeline, said first periodic time interval being different from a second periodic time interval for periodically displaying patient data on said timeline in a second time duration exclusive of said first time duration;
enabling a user to select a start time and end time identifying said first time duration within said timeline;
acquiring first and second patient data substantially at said first and second periodic time intervals and in said first and second time durations, respectively;
displaying said acquired first and second patient data at said first periodic time interval during said first time duration in a display image together with data representing said timeline; and
displaying said acquired first and second patient data at said second periodic time interval during said second time duration in a display image together with data representing said timeline.

2. The method of claim 1 wherein
the step of enabling a user to select a time interval further comprises a step of displaying a list of selectable time intervals.

3. The method of claim 2 wherein the list of selectable time intervals comprises
at least one or more of the following time intervals: 1) 3 minutes; 2) 5 minutes; 3) 15 minutes; 4) 30 minutes; 5) 1 hour; 6) 2 hours; and 7) 4 hours.

4. The method of claim 1 wherein
the step of enabling a user to select a start time further comprising a step of displaying a list of allowable start time choices based on a predetermined rule.

5. The method of claim 4 wherein
the step of enabling a user to select an end time further comprising a step of displaying a list of allowable end time choices based on a predetermined rule.

6. The method of claim 4 wherein the predetermined rule comprises one or more of the following restrictions: 1) the allowable start time occurs on the hour; 2) the allowable start time currently appears on an associated flow sheet; 3) the allowable start time occurs on an even hour, when the selected time interval is 2-hour; and 4) the allowable start time needs to be in the set of (0, 4:00, 8:00, 12:00, 16:00 and 20:00), when the selected time interval is 4-hour.

7. The method of claim 1 further comprising
enabling a user via a user interface display image, to select said second periodic time interval for periodically displaying patient data in said second time duration.

8. The method of claim 7 wherein the second time interval is selectable by a user.

9. The method of claim 4 further comprising a step of displaying a default start time.

10. The method of claim 5 further comprising a step of displaying a default end time.

11. The method of claim 1 further comprising:
determining if the selected time interval affects data that has been acted on via the patient data screen; and
disallowing the change to the selected time interval for the timeline in response to the above determining step.

12. A system for processing data, comprising:
a processor for
enabling a user, via a user interface display image, to select a first periodic time interval for periodically displaying patient date in a first time duration on a timeline, said first periodic time interval being different from a second periodic time interval for periodically displaying patient data on said timeline in a second time duration exclusive of said first time duration;

enabling a user to select a start time and end time identifying a said first time duration within the timeline;

acquiring first and second patient data substantially at said first and second periodic time intervals and in said first and second time durations, respectively;

applying the selected time interval to the timeline for the duration identified by the selected start time and end time; and a display for displaying said acquired first and second patient data at said first periodic time interval during said first time duration in a display image together with data representing said timeline and displaying said acquired first and second patient data at said second periodic time interval during said second time duration in a display image together with data representing said timeline.

13. The system of claim 12 wherein the time interval is selected by using a displayed list of selectable time intervals.

14. The system of claim 13 wherein the displayed list of selectable time intervals comprises at least one or more of the following time intervals: 1) 3 minutes; 2) 5 minutes; 3) 15 minutes; 4) 30 minutes; 5) 1 hour; 6) 2 hours; and 7) 4 hours.

15. The system of claim 12 wherein the start time is selected by using a displayed list of allowable start time choices based on a predetermined rule.

16. The system of claim 12 wherein the end time is selected by using a displayed list of allowable end time choices based on a predetermined rule.

17. The system of claim 15 wherein the predetermined rule comprises one or more of the following restrictions: 1) the allowable start time occurs on the hour; 2) the allowable start time currently appears on an associated flow sheet; 3) the allowable start time occurs on an even hour, when the selected time interval is 2-hour; and 4) the allowable start time needs to be in the set of (0, 4:00, 8:00, 12:00, 16:00 and 20:00), when the selected time interval is 4-hour.

18. The system of claim 12 wherein the processor further enables the user, via a user interface display image, to select the second periodic time interval in the second duration.

19. The system of claim 18 wherein the second time interval is selected from a list of time intervals.

20. The system of claim 15 wherein the displayed list of allowable start time choices comprises a default start time.

21. The system of claim 15 wherein the displayed list of allowable end time choices comprises a default end time.

22. The system of claim 18 wherein the processor further allows the user to select a second start time and a second end time for the selected second duration.

23. A method of processing data, comprising the steps of:

receiving a time interval change request including a first periodic time interval for periodically displaying patient date in a first time duration on a timeline, the first periodic time interval being different from a second periodic time interval for periodically displaying patient data on said timeline in a second time duration exclusive of said first time duration;

determining allowable start time and end time choices in response to the time interval change request;

displaying default start time and end time;

displaying allowable start time and end time choices in response to another user request;

selecting a start time and end time identifying the first time duration from the displayed choices;

applying the first periodic time interval to the first time duration between the selected start time and end time;

acquiring first and second patient data substantially at the first and second periodic time intervals and in said first and second time durations, respectively; and updating the acquired first and second patient data at the first periodic time interval during the first time duration in a display image together with data representing said timeline and updating the acquired first and second patient data at said second periodic time interval during said second time duration in a display image together with data representing said timeline in response to applying the time interval change.

24. The method of claim 23 wherein the data comprises a patient flow sheet.

25. The method of claim 11 wherein the data has been acted on by at least one of the following actions: 1) data has been changed by a user; 2) data has been accepted by a user; and 3) data has been entered by a user.

* * * * *